United States Patent
Dannenmaier et al.

(10) Patent No.: US 8,142,383 B2
(45) Date of Patent: Mar. 27, 2012

(54) FLUID DISTRIBUTION MODULE AND EXTRACORPOREAL BLOOD CIRCUIT INCLUDING SUCH A MODULE

(75) Inventors: Jürgen Dannenmaier, Balingen (DE); Hermann Goehl, Bisingen (DE); Thomas Ertl, Bisingen (DE); Jacques Chevallet, Serezin du Rhône (FR); Francesco Ribolzi, Modena (IT)

(73) Assignee: Gambro AB (SE)

( * ) Notice: Subject to any disclaimer, the term of this patent is extended or adjusted under 35 U.S.C. 154(b) by 1078 days.

(21) Appl. No.: 10/595,705

(22) PCT Filed: Oct. 29, 2004

(86) PCT No.: PCT/EP2004/012277
§ 371 (c)(1),
(2), (4) Date: Apr. 12, 2007

(87) PCT Pub. No.: WO2005/044340
PCT Pub. Date: May 19, 2005

(65) Prior Publication Data
US 2007/0269340 A1 Nov. 22, 2007

(30) Foreign Application Priority Data

Nov. 7, 2003 (EP) .................................... 03025640
Nov. 24, 2003 (EP) .................................... 03026854
Nov. 24, 2003 (EP) .................................... 03026855

(51) Int. Cl.
*A61M 37/00* (2006.01)
*A61M 1/00* (2006.01)
(52) U.S. Cl. ....... 604/6.09; 604/6.1; 604/6.14; 604/126; 422/45
(58) Field of Classification Search ........ 604/4.01–6.16, 604/7–10, 19–35, 122–126; 422/44–48; 210/645
See application file for complete search history.

(56) References Cited

U.S. PATENT DOCUMENTS 4,227,420 A  10/1980  Lamadrid
(Continued)

FOREIGN PATENT DOCUMENTS

DE  4027531 C1  7/1991
(Continued)

OTHER PUBLICATIONS

WIPO, International Search Report, for PCT No. PCT/EP2004/012277, Published May 19, 2005, 3pgs.
(Continued)

*Primary Examiner* — Tatyana Zalukaeva
*Assistant Examiner* — Philip R Wiest
(74) *Attorney, Agent, or Firm* — Finnegan, Henderson, Farabow, Garrett & Dunner, LLP

(57) ABSTRACT

A fluid distribution module (1) for causing and monitoring the circulation of fluids from and to a patient through an extracorporeal blood treatment device, comprises a degassing device (11) connected to a connecting structure (10). The degassing device (11) comprises a first chamber (12) having a lower inlet (13) for a liquid and a second chamber (14) having an upper opening (79) closed by a hydrophobic membrane (78) and an outlet (15) for discharging the liquid. The connecting structure (10) has at least a first and a second conduits (20, 21) defined therein, wherein the first conduit (20) comprises a first end for connection to a discharge tube (7) from the treatment device and a second end connected to the inlet (13) of the first chamber (12) of the degassing device (11), and the second conduit (21) comprises a first end connected to the outlet (15) of the second chamber (14) of the degassing device (11) and a second end for connection to a blood return tube (6) to a patient.

37 Claims, 8 Drawing Sheets

U.S. PATENT DOCUMENTS

| | | | |
|---|---|---|---|
| 4,231,871 A | 11/1980 | Lipps et al. | |
| 4,263,808 A | 4/1981 | Bellotti et al. | |
| 4,287,059 A | 9/1981 | Kume et al. | |
| 4,293,413 A | 10/1981 | Schnell | |
| 4,344,777 A | 8/1982 | Siposs | |
| 4,345,999 A | 8/1982 | Sigdell et al. | |
| 4,368,118 A | 1/1983 | Siposs | |
| 4,379,452 A | 4/1983 | DeVries | |
| 4,412,916 A | 11/1983 | Kell | |
| 4,433,971 A * | 2/1984 | Lindsay et al. | 604/122 |
| 4,436,620 A | 3/1984 | Bellotti et al. | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,493,693 A | 1/1985 | Bilstad et al. | |
| 4,582,598 A | 4/1986 | Bilstad et al. | |
| 4,605,503 A | 8/1986 | Bilstad et al. | |
| 4,617,115 A | 10/1986 | Vantard | |
| 4,623,450 A | 11/1986 | Vantard et al. | |
| 4,666,598 A | 5/1987 | Heath et al. | |
| 4,676,467 A | 6/1987 | Palsulich | |
| 4,698,207 A * | 10/1987 | Bringham et al. | 422/46 |
| 4,765,888 A | 8/1988 | Barthe et al. | |
| 4,770,787 A | 9/1988 | Heath et al. | |
| 4,798,090 A | 1/1989 | Heath et al. | |
| 4,806,135 A | 2/1989 | Siposs | |
| 4,824,339 A | 4/1989 | Bainbridge et al. | |
| 5,011,469 A * | 4/1991 | Buckberg et al. | 604/6.11 |
| 5,200,090 A | 4/1993 | Ford et al. | |
| 5,441,636 A | 8/1995 | Chevallet et al. | |
| 5,468,388 A | 11/1995 | Goddard et al. | |
| 5,643,191 A * | 7/1997 | Buckberg et al. | 604/6.13 |
| 5,707,431 A * | 1/1998 | Verkaart et al. | 96/177 |
| 5,744,047 A | 4/1998 | Gsell et al. | |
| 5,837,905 A * | 11/1998 | Strauss et al. | 73/861.63 |
| 5,849,065 A | 12/1998 | Wojke | |
| 6,176,903 B1 | 1/2001 | Wamsiedler | |
| 6,206,954 B1 | 3/2001 | Schnell et al. | |
| 6,361,518 B1 | 3/2002 | Brierton et al. | |
| 6,582,386 B2 | 6/2003 | Min et al. | |
| D479,320 S | 9/2003 | O'Mahony et al. | |
| 2003/0138349 A1 | 7/2003 | Robinson et al. | |

FOREIGN PATENT DOCUMENTS

| | | |
|---|---|---|
| EP | 0245782 A2 | 11/1987 |
| EP | 0292445 A1 | 11/1988 |
| EP | 0591896 A2 | 4/1994 |
| FR | 2513884 | 4/1983 |
| WO | WO-00/25843 A1 | 5/2000 |

OTHER PUBLICATIONS

WIPO, International Search Report, for PCT No. PCT/EP2004/012528 Published May 19, 2005, 4pgs.

WIPO, International Search Report, for PCT No. PCT/EP2004/011707 Published May 19, 2005, 2pgs.

WIPO, International Search Report, for PCT No. PCT/EP2004/012372 Published Jun. 16, 2005, 3pgs.

EPO, European Search Report, Application No. 1529545, Published Jun. 1, 2005, 3pgs.

EPO, European Search Report, Application No. 1530995, Published May 18, 2005, 2pgs.

EPO, European Search Report, Application No. 1532994, Published May 25, 2005, 3pgs.

* cited by examiner

FLUID DISTRIBUTION MODULE AND EXTRACORPOREAL BLOOD CIRCUIT INCLUDING SUCH A MODULE

The present invention relates to a fluid distribution module for causing and monitoring the circulation of fluids to and from a patient, and to an extracorporeal blood circuit including such a module.

Extracorporeal blood circuits are used in various medical treatments in which the blood of a patient is dynamically treated outside of the patient's body in a blood treatment device. In this type of treatments, an extracorporeal blood circuit is used to continuously convey a fraction of the blood of the patient to the blood treatment device and to return it to the patient once treated.

Examples of such medical treatments are hemodialysis, hemofiltration and hemodiafiltration, which are used for palliating kidney failure.

In these treatments, the device in which the blood of a patient is treated is a hemodialyzer/hemofilter, i.e. a filter made of biologically neutral materials, including a semipermeable membrane having specific diffusive and convective properties.

A conventional hemodialyzer/hemofilter comprises a first and a second compartments separated by a semi-permeable membrane composed of a bundle of hollow fibers. The first compartment has an inlet and an outlet for the circulation of blood therethrough and the second compartment has an outlet for draining a liquid (e.g. plasma water, used dialysis liquid) and an inlet when the treatment (e.g. hemodialysis) requires the circulation of a treatment liquid (e.g. a dialysis liquid) in the second compartment. The membrane is enclosed in an elongated tubular housing closed at both ends by an end-cap having a nozzle used as an inlet/outlet port for the first compartment.

In the above treatments, blood is withdrawn from the patient, flown through the first compartment of the filter, and returned to the patient. In hemodialysis, a dialysis liquid is simultaneously flown though the second compartment of the filter and the metabolic wastes (urea, creatinine) contained in blood migrate by diffusion through the membrane into the second compartment. In hemofiltration, a pressure difference is created across the membrane so that plasma water flows through the membrane into the second compartment of the filter. Here, metabolic wastes migrate by convection into the second compartment. In order to compensate for the loss of bodily fluid, the patient is simultaneously infused a sterile substitution solution. Hemodiafiltration is a combination of hemodialysis and hemofiltration, and, in this treatment, a dialysis liquid is flown through the second compartment and a substitution liquid is infused into the patient.

A machine for performing any of the above treatments comprises a peristaltic pump for withdrawing blood from a patient through a so-called "arterial" line connected at one end to the vascular circuit of the patient and at the other end to the inlet of the first compartment of a filter, for pumping blood into the filter, and for returning blood to the patient through a so-called "venous" line connected at one end to the outlet of the first compartment of the filter and at the other end to the vascular circuit of the patient. The treatment machine also usually comprises a first blood pressure sensor for measuring the pressure of blood in the arterial line upstream of the pump, a second blood pressure sensor for measuring the pressure of blood in the arterial line downstream of the pump, a third pressure sensor for measuring the pressure of blood in the venous line, a bubble detector for detecting air bubbles in the venous line and a clamp for closing the venous line, for example when air bubbles are detected by the bubble detector.

A conventional extracorporeal blood circuit comprises an arterial line and a venous line.

An arterial line typically comprises the following components connected together by segments of flexible tubes: a first Luer connector for connection to an arterial cannula, an arterial bubble trap, a pump hose for cooperating with the rotor of the peristaltic pump of the treatment machine, and a second Luer connector for connection to the inlet of the first compartment of the filter.

A venous line typically comprises the following components connected together by segments of flexible tubes: a first Luer connector for connection to the outlet of the first compartment of the filter, a venous bubble trap, and a second Luer connector for connection to a venous cannula. Usually, the first and third pressure sensors of the machine are connected to the arterial and venous bubble trap respectively, when the treatment machine, the arterial line, the venous line and the filter are assembled in view of a treatment.

A conventional bubble trap is basically an elongated container that, in use, is held vertically. The container has an inlet and an outlet for blood that are arranged so as not to be adjacent. It comprises also, in an upper location, a pressure measuring port for connection to a pressure sensor, an infusion port for infusing a liquid (e.g. a drug or a sterile saline solution) and an injection port for adding or removing air into or from the bubble trap so as to adjust the level of blood therein. In use, the bubble trap contains a volume of blood in a lower part that transiently stagnates therein so as to allow gas bubbles and micro bubbles escape by gravity and gather in an upper part of the container full of air. In a conventional bubble trap, there is therefore always an interface blood-air.

Besides the fact that, in order to properly operate, conventional bubble traps must contain a certain volume of blood (which conflicts with the desirable minimization of the volume of blood outside of the body during extracorporeal blood treatments), their use is limited to relatively short treatment sessions because of the blood clotting resulting from the permanent blood-air interface. In this respect, they are adapted to chronic treatment (a treatment session for a chronic patient usually lasts about four hours), but they cannot be used for intensive care treatment (the treatment of an acute patient can last several days).

An object of the invention is to design an extracorporeal blood circuit without blood-air interface in operation and having an internal volume substantially less than the internal volume of a conventional blood extracorporeal circuit.

Another object of the invention is to design an extracorporeal blood circuit that is easy to connect to a treatment machine.

According to the invention, a fluid distribution module for an extracorporeal blood circuit comprises:
  a degassing device having a longitudinal axis, comprising:
    a first chamber having an inlet for a liquid; and
    a second chamber having an opening closed by a hydrophobic membrane and an outlet for discharging the liquid,
wherein the first chamber partially extends within the second chamber and communicates therewith by an upper passageway, and the second chamber comprises a upstream portion extending above the passageway and a downstream portion extending below the passageway, and
  a connecting structure having at least a first and a second conduits defined
therein, wherein:

the first conduit comprises a first end for connection to a discharge tube from a treatment device and a second end connected to the inlet of the first chamber of the degassing device, and the second conduit comprises a first end connected to the outlet of the second chamber of the degassing device and a second end for connection to a blood return tube to a patient.

Additional or alternative features of the invention are as follows:

The connecting structure further comprises a third conduit defined therein having a first end for connection to a post-dilution infusion tube and a second end connected to the first conduit.

The connecting structure further comprises a fourth and a fifth conduits defined therein, wherein the fourth conduit comprises a first end for connection to a blood withdrawal tube from a patient and a second end for connection to a first end of a pump hose of a peristaltic pump, and the fifth conduit comprises a first end for connection to a second end of the pump hose of a peristaltic pump and a second end for connection to a supply tube to a blood treatment device.

The connecting structure further comprises a sixth conduit defined therein having a first end for connection to an anti-coagulant tube and a second end connected to the fifth conduit.

The connecting structure further comprises a seventh conduit defined therein having a first end for connection to a pre-dilution infusion tube and a second end connected to the fourth conduit.

The connecting structure further comprises a first pressure-measuring chamber having a first and a second compartments separated by a flexible membrane, wherein the first compartment is connected to the first conduit, and the second compartment has a measuring port for connection to a gas pressure sensor.

The connecting structure further comprises a second pressure-measuring chamber having a first and a second compartments separated by a flexible membrane, wherein the first compartment is connected to the fourth conduit, and the second compartment has a measuring port for connection to a gas pressure sensor.

The connecting structure further comprises a third pressure-measuring chamber having a first and a second compartments separated by a flexible membrane, wherein the first compartment is connected to the fifth conduit, and the second compartment has a measuring port for connection to a gas pressure sensor.

The measuring ports of the first, second, and third pressure-measuring chambers have a central axis (y, z, w), and the central axes of at least two of the measuring ports are substantially parallel.

The measuring ports of at least two of the first, second, and third pressure-measuring chambers are substantially perpendicular to a longitudinal axis (x) of the degassing device.

The connecting structure has a periphery and comprises at least one socket connected thereto, wherein the socket has a recess for receiving one end of a tube and forms one end of one of the conduits defined within the connecting structure.

The connecting structure comprises a first and second sockets forming the second end of the fourth conduit and the first end of the fifth conduit, wherein the first and second sockets are so positioned that a pump hose having both ends received in the two sockets forms a loop that laterally extends within a plan from the connecting structure.

An extracorporeal blood circuit including the fluid distribution module according to the invention presents several advantages. First, it is compact and allows for a significant reduction of the extracorporeal blood volume that is needed in extracorporeal blood treatments. Second, it does not require any specific activity for its mounting on a treatment machine nor for its setting in use (in particular, no adjustment of the level of the air-blood interface is needed in the degassing device, since the degassing device is full of liquid when in operation). Third, since the degassing device operates without air-blood interface, the integrated blood circuit is particularly adapted to long lasting treatments (e.g. continuous renal replacement therapies).

Other additional or alternative features of the invention are as follows:

The first chamber of the degassing device has a downstream portion having a cross-section selected with respect to a maximal blood flow rate in an extracorporeal blood circuit connected to the degassing device so that the velocity of blood in the downstream portion of the first chamber is less than a predetermined velocity.

The cross-section of the downstream portion of the first chamber is selected with respect to a maximal blood flow rate in an extracorporeal blood circuit of about 500 ml/min so that the velocity of blood in the downstream portion of the first chamber is less than about 3 m/min.

The cross-section of the second chamber of the degassing device at the level of the passageway is selected so that the ratio of the velocity of blood within a downstream portion of the first chamber to the velocity of blood within the second chamber at the level of the passageway is more than a determined value.

The cross-section of the second chamber of the degassing device at the level of the passageway is selected so that the ratio of the velocity of blood within the downstream portion of the first chamber to the velocity of blood within the second chamber at the level of the passageway is at least about 2.

The downstream portion of the second chamber of the degassing device asymmetrically surrounds an upper part of the first chamber.

The first chamber comprises a downstream portion having a cylindrical wall extending along a longitudinal axis (x) of the degassing device, and the downstream portion of the second chamber comprises a cylindrical wall partially surrounding the cylindrical wall of the first chamber and a bottom wall that is beveled with respect to the longitudinal axis (x) of the degassing device.

The cylindrical wall of the first chamber and the cylindrical wall of the second chamber are concentric.

The passageway has a lesser cross-section than a cross-section of the second chamber so that a flow of liquid from the first chamber into the second chamber decreases within the second chamber.

The first chamber, the second chamber and the passageway are arranged with respect to each other so that a flow pattern of a liquid flowing through the degassing device comprises a component that is tangential to the hydrophobic membrane.

The flow pattern of a liquid flowing through the degassing device comprises an umbrella like component.

The first chamber, the second chamber and the passageway are arranged with respect to each other so that a liquid flowing through the degassing device keeps gas bubbles in motion along an inner surface of the hydrophobic membrane.

The first chamber comprises a downstream portion having a cross-section that is substantially the same as the cross-section of the passageway between the first and the second chambers.

The downstream portion of second chamber forms an overflow for a liquid flowing from the first chamber into the second chamber.

The upstream portion of the second chamber has a decreasing cross-section, with a larger cross-section that is substantially level with the passageway and a smaller cross-section that is substantially level with the hydrophobic membrane.

The outlet of the degassing chamber opens in the second chamber at a lowest point thereof.

The blood-degassing device that is part of the fluid distribution module according to the invention is very efficient and remains efficient over time. Also its allows for a compact design, i.e. a small internal volume. For example, It is possible to design such degassing device with a total internal volume that is about half of the blood volume in conventional bubble traps.

Another object of the invention is an extracorporeal blood circuit comprising:
a fluid distribution module as defined above;
a pump hose having a first end connected to the second end of the fourth conduit and a second end connected to the a first end of the fifth conduit;
a blood withdrawal tube connected to a first end of the fourth conduit;
a supply tube to a blood treatment device connected to the second end of the fifth conduit;
a discharge tube from a treatment device connected to the first end of the first conduit; and
a blood return tube connected to the second end of the second conduit.

Other features and advantages of the invention will appear on reading the detailed description that follows. Reference will be made to the appended drawings in which.

Figure 1:
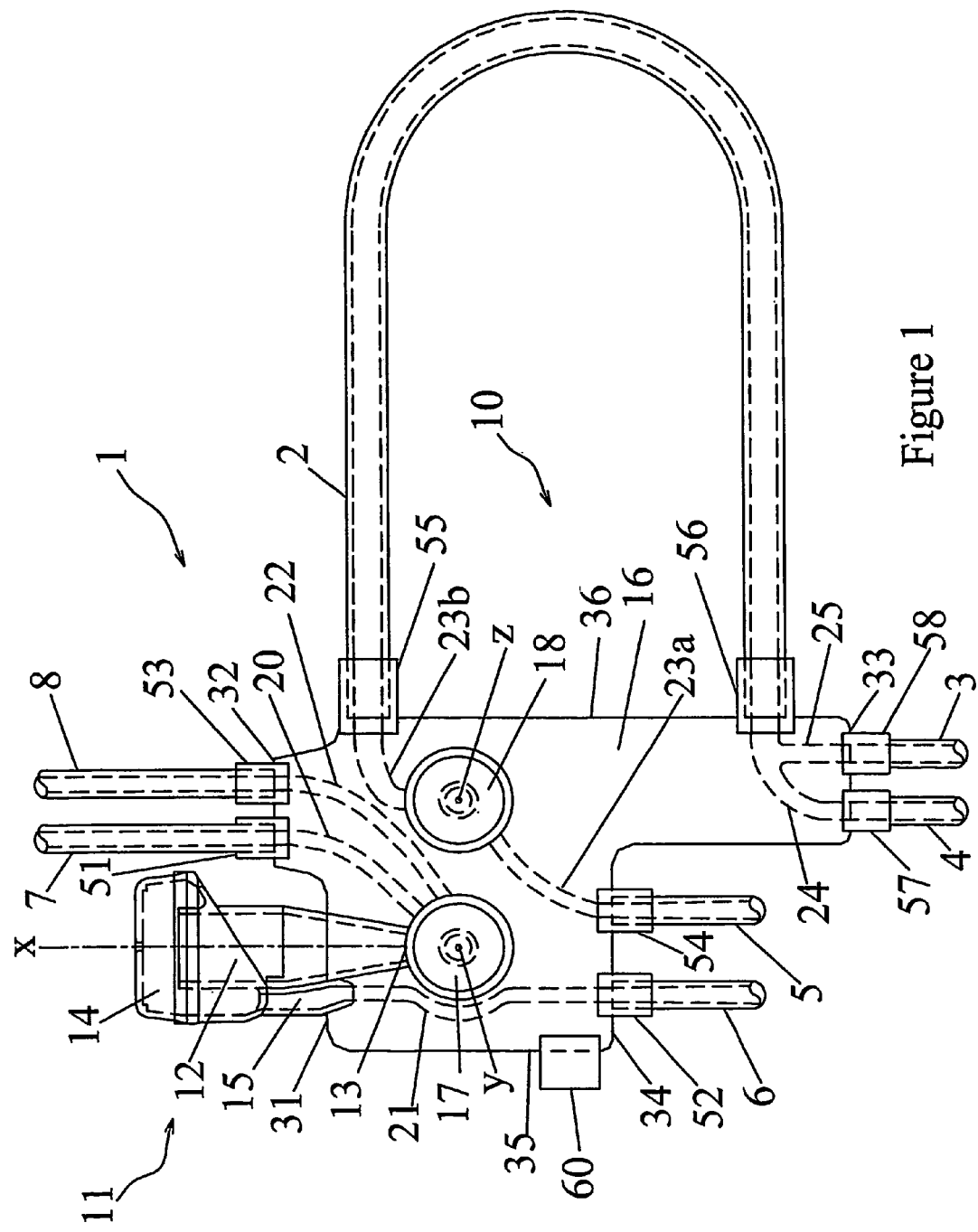
FIG. 1 is a partial front view of a first embodiment of the extracorporeal blood circuit according to the invention.

The extracorporeal blood circuit represented in FIG. 1 comprises a fluid distribution module 1, to which are connected a pump hose 2 and tubes 3 to 8 for conveying various liquids to and from the fluid distribution module 1.

The fluid distribution module 1 comprises a connecting structure 10 and a degassing device 11 connected thereto. The degassing device 11 has a central longitudinal axis x, which is substantially vertical when the fluid distribution module 1 is in an operational position. The degassing device 11 comprises a first chamber 12 having an inlet 13 for a liquid, and a second chamber 14 in communication with the first chamber 12, fitted with an outlet port 15 for discharging the liquid. The degassing device 11 will be described in greater detail with respect to FIGS. 5 to 7.

The connecting structure 10 comprises a substantially flat body 16, a first pressure-measuring chamber 17 and a second pressure-measuring chamber 18 made in part integral with the flat body 16, and six conduits 20, 21, 22, 23, 24, 25 made integral with the flat body 16.

The flat body 16 comprises: a front side (apparent on the figure); a rear side opposite to the front side; an upper edge including a lower rim 31 and an upper rim 32; a lower edge including a lower rim 33 and an upper rim 34; a left lateral edge 35; and a right lateral edge 36. The lateral edges 35, 36 are parallel and perpendicular to the lower and upper rims 31, 32, 33, 34 of the lower and upper edges.

Each pressure-measuring chambers 17, 18 comprises a disk-shaped casing having a central axis y, z; the central axis y of the first pressure-measuring chamber 17 intersects the central longitudinal axis x of the degassing device 11; the central axes y, z are parallel and lie in the same substantially horizontal plane when the fluid distribution module 1 is in an operational position.

Figure 4:
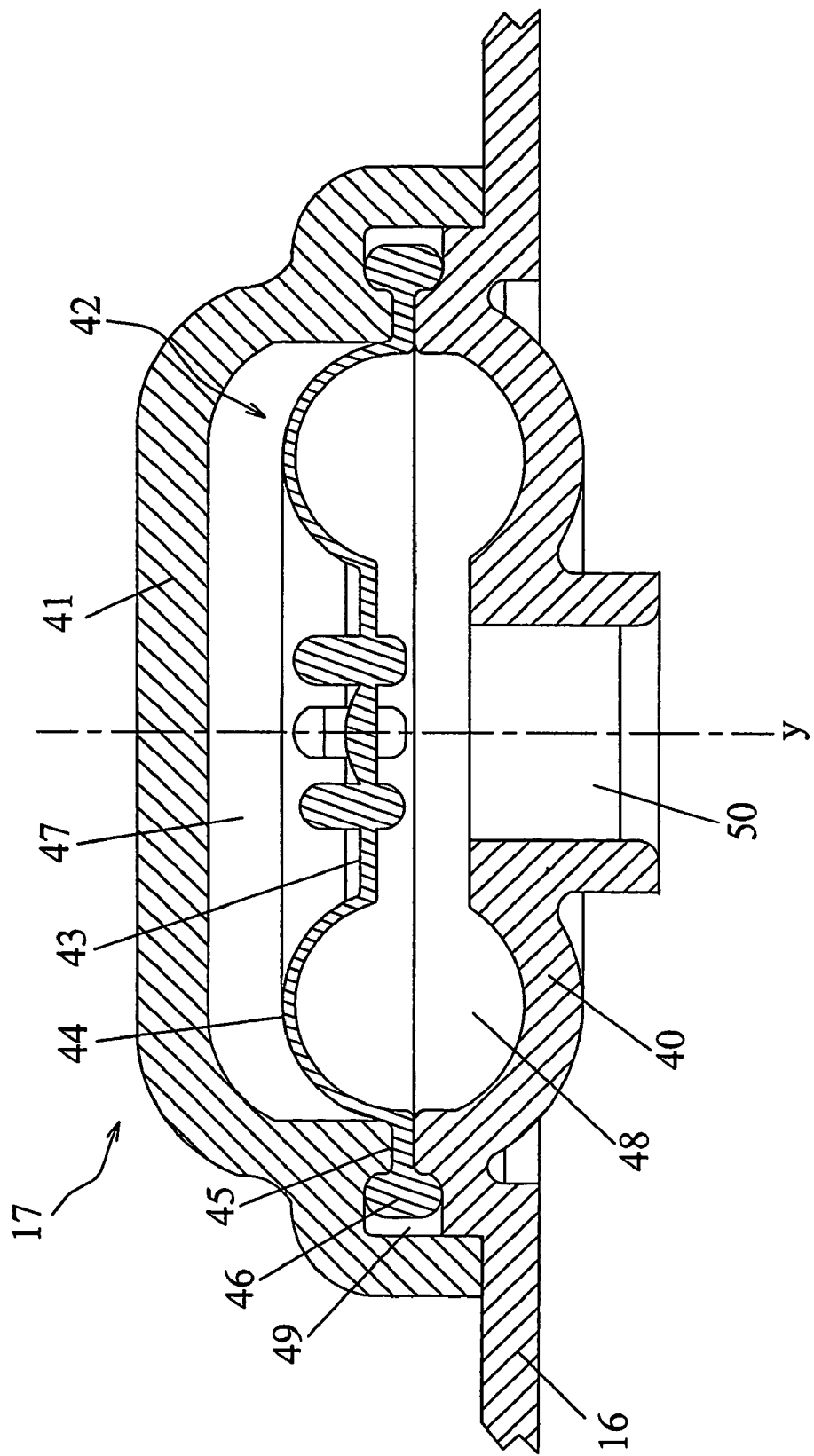
FIG. 4 is a cross section view of a blood pressure-measuring chamber for the extracorporeal blood circuit according to the invention.

As apparent in FIG. 4, the disk-shaped casing of the first pressure-measuring chamber 17 comprises a base portion 40, (integral with the flat body 16 of the connecting structure 10) and a lid 41 that are so designed as to secure at their periphery a circular flexible membrane 42 dividing the interior of the casing into a blood compartment 47 and an air compartment 48. The membrane 42 comprises a central flat circular portion 43, connected to an annular portion 44 having a partly toroid surface, connected in turn to a narrow peripheral flat annular portion 45, finally connected to a peripheral O-ring 46. The peripheral areas of the base portion 40 and of the lid 41 are so shaped as to define between them a ring space 49 in which the O-ring 46 surrounding the membrane 42 can be received and squeezed so as to insure a tight separation between the two compartments 47, 48. The blood compartment 47 comprises an inlet port and an outlet port (not shown). The air compartment 48 comprises a measurement port 50 for connection to a pressure sensor of a dialysis machine.

The measurement ports 50 of the pressure measuring chambers 17, 18 are opening on the rear side of the flat body 16 of the connecting structure 10.

The blood pressure-measuring chamber represented in FIG. 4 is adapted to the measurement of positive blood pressures and that is why the membrane 42 is mounted in the casing so that its convexity faces the blood compartment 47 (this allows for a maximal deformation of the membrane). In a blood pressure-measuring chamber adapted to negative pressure (chamber 18), the membrane 42 is mounted in the casing so that its convexity faces the air compartment 48.

The conduits made integral with the flat body 16 of the connecting structure 10 include:
A first conduit 20 having a first end opening at the upper rim 32 of the upper edge of the flat body 16, and a second end connected to a first inlet of the blood compartment 47 of the first (positive) pressure-measurement chamber 17. The first end of the first conduit 20 is fitted with a socket 51 in which a first end of a blood discharge tube 7 is received and glued. The blood discharge tube 7 has a second end fitted with a Luer connector for connection to the blood outlet of a blood treatment device (e.g. a hemodialyzer/hemofilter). It results from this arrangement, that the pressure-measurement chamber 17 is used to measure the blood pressure downstream of a blood treatment device (usually referred to as the "venous pressure"), in the portion of the extracorporeal blood circuit returning the treated blood to the patient.

A second conduit 21 having a first end opening at the lower rim 31 of the upper edge of the flat body 16, and a second end opening at the upper rim 34 of the lower edge of the flat body 16. The first end of the second conduit 21 is connected to the outlet port 15 of the second chamber 14 of the degassing device 11. The second end of the second conduit 21 is fitted with a socket 52 in which a first end of a blood return tube 6 (usually referred to as the "venous line") is received and glued. The blood return tube 6 has a second end fitted with a Luer connector for connection to a fistula needle.

A third conduit 22 having a first end opening at the upper rim 32 of the upper edge of the flat body 16, and a second end connected to a second inlet of the blood compartment 47 of the positive pressure-measurement chamber 17. The first end of the third conduit 22 is fitted with a socket 53 in which a first end of a post-dilution infusion tube 8 is received and glued.

A fourth conduit 23 comprising an upstream portion 23a and a downstream portion 23b.

The upstream portion 23a has a first end opening at the upper rim 34 of the lower edge of the flat body 16, and a second end connected to an inlet of the blood compartment 47 of the second (negative) pressure-measurement chamber 18. The first end of the upstream portion 23a is fitted with a socket 54 in which a first end of a blood withdrawal tube 5 (usually referred to as the "arterial line") is received and glued. The blood withdrawal tube 5 has a second end fitted with a Luer connector for connection to a fistula needle.

The downstream portion 23b has a first end connected to an outlet of the blood compartment 47 of the second (negative) pressure-measurement chamber 18, and a second end opening at the right edge 36 of the flat body 16. The second end of the downstream portion 23b is fitted with a socket 55 in which a first end of the pump hose 2 is received and glued. The socket 55 is close to the upper edge of the connecting structure 10.

It results from this arrangement, that the pressure-measurement chamber 18 is used to measure the blood pressure upstream of a blood pump (usually referred to as the "arterial pressure") in the portion of the extracorporeal blood circuit withdrawing the blood to be treated from the patient.

A fifth conduit 24 has a first end opening at the right edge 36 of the flat body 16, and a second end opening at the lower rim 33 of the lower edge of the flat body 16. The first end of the fifth conduit 24 is fitted with a socket 56 in which a second end of the pump hose 2 is received and glued. The socket 56 is close to the lower rim 33 of the lower edge of the connecting structure 10. The second end of the fifth conduit 24 is fitted with a socket 57 in which a first end of a blood supply tube 4 is received and glued. The blood supply tube 4 has a second end fitted with a Luer connector for connection to the blood inlet of a blood treatment device (e.g. a hemodialyzer/hemofilter).

The sockets 55 and 56 in which the first and second ends of the pump hose 2 are respectively received and glued are so spaced apart and oriented that the pump hose 2 substantially lies in the same plane as the flat body 16 of the connecting structure 10 and forms a loop adapted to cooperate with the rotor of a peristaltic pump of a blood treatment machine.

A sixth conduit 25 has a first end connected to the fifth conduit 24, and a second end opening at the lower rim 33 of the lower edge of the flat body 16. The second end of the sixth conduit 25 is fitted with a socket 58 in which a first end of an anti-coagulant tube 3 is received and glued. The anti-coagulant tube 3 has a second end fitted with a Luer connector for connection to the outlet of an anti-coagulant pump.

The connecting structure 10 further comprises securing means for its releasable connection to a blood treatment machine. The securing means includes the two sockets 55, 56 that protrude outwardly from the right edge 36 of the connecting structure 10 and a stud 60 that protrudes outwardly from the left edge 35 of the connecting structure 10. These three protruding elements are intended to cooperate with three corresponding clamps on the front panel of a blood treatment machine.

Figure 2:
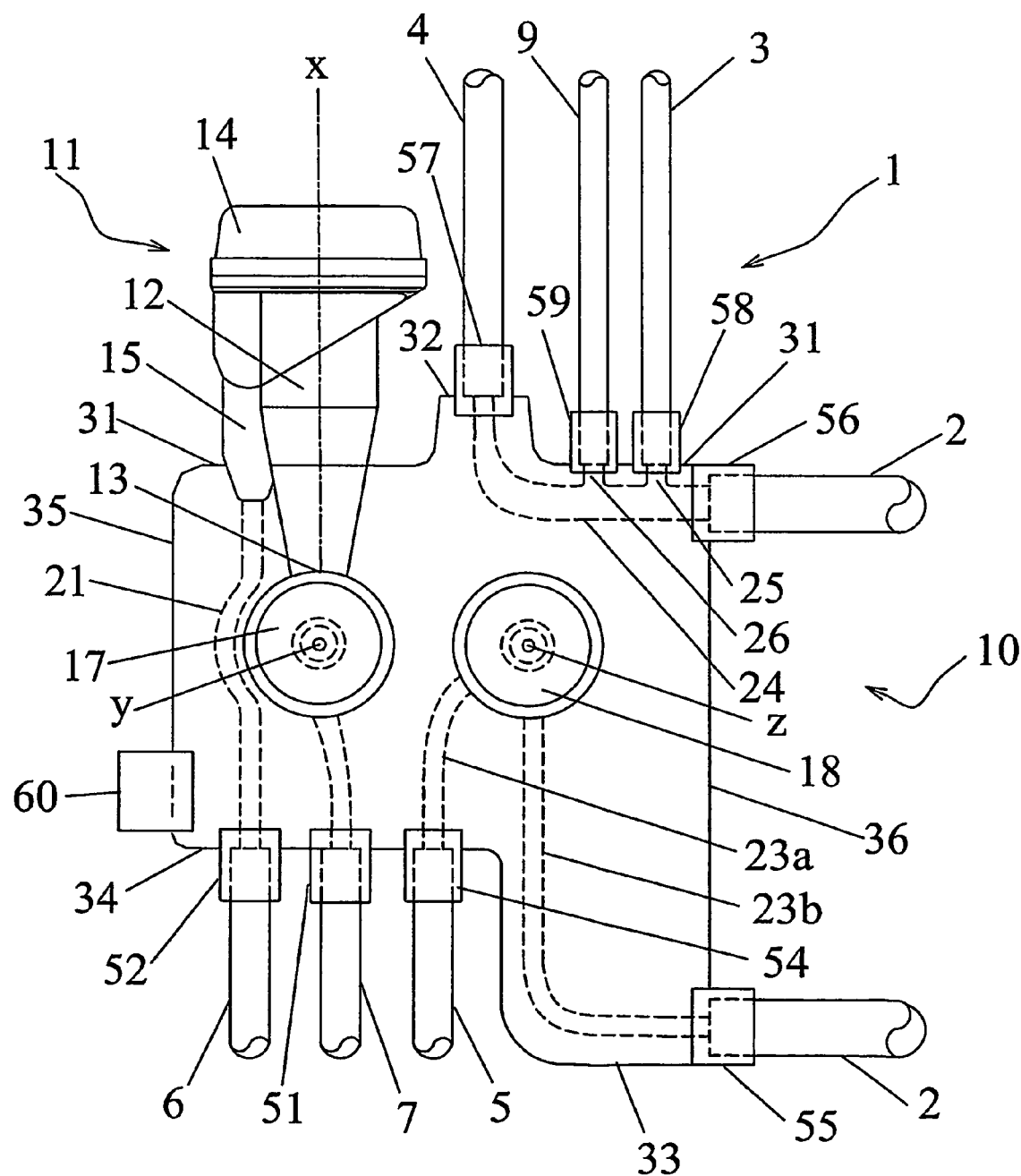
FIG. 2 is a partial front view of a second embodiment of the extracorporeal blood circuit according to the invention.

The extracorporeal blood circuit represented in FIG. 2 differs from the extracorporeal blood circuit represented in FIG. 1 essentially in that:

The first end of the first conduit 20 opens at the upper rim 34 of the lower edge of the flat body 16;

The second end (socket 55) of the downstream portion 23b of the fourth conduit opens at the right edge 36 of the flat body 16, close to the lower rim 33 of the lower edge of the connecting structure 10.

The first end (socket 56) of the fifth conduit 24 opens at the right edge 36 of the flat body 16, close to the lower rim 31 of the upper edge of the connecting structure 10 (as a result, the socket 56 is above the socket 55); the second end (socket 57) of the fifth conduit 24 opens at the upper rim 32 of the upper edge of the flat body 16.

A seventh conduit 26 has a first end connected to the fifth conduit 24, and a second end opening at the lower rim 31 of the upper edge of the flat body 16. The second end of the seventh conduit 26 is fitted with a socket 59 in which a first end of a pre-dilution infusion tube 9 is received and glued.

Also the connecting structure 10 of the extracorporeal blood circuit of FIG. 2 does not comprise a third conduit for post-dilution infusion.

Figure 3:
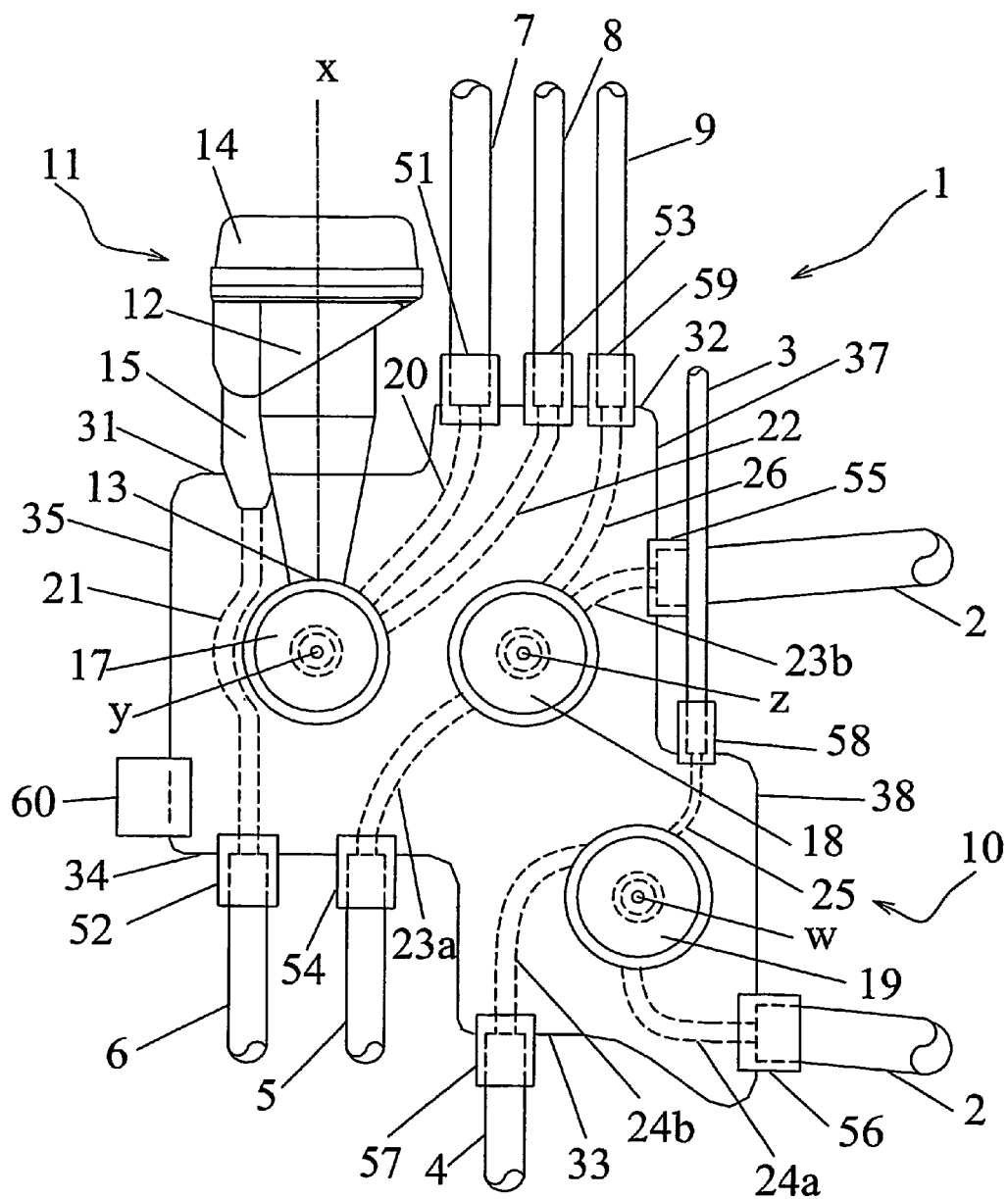
FIG. 3 is a partial front view of a third embodiment of the extracorporeal blood circuit according to the invention.

The extracorporeal blood circuit represented in FIG. 3 differs from the extracorporeal blood circuit represented in FIG. 1 essentially in that:

The connecting structure 10 comprises a third pressure-measuring chamber 19 made in part integral with the flat body 16. The third pressure-measuring chamber 19 is positioned with respect to the flat body 16 of the connecting structure 10 like the two other pressure-measuring chambers 17, 18, namely with its central axis w perpendicular to the flat body 16 and its measuring port 50 opening on the rear side of the flat body 16. The third pressure-measuring chamber 19 is similar to the pressure-measuring chamber 17 connected to the blood return tube 6, in as much as it is used to measure a positive pressure, namely the blood pressure immediately downstream of the pump hose 2. The fifth conduit 24 comprises an upstream portion 24a connecting the second end of the pump hose 2 to an inlet of the blood chamber of the pressure-measuring chamber 19, and a downstream portion 24b connecting an outlet of the blood chamber of the pressure-measuring chamber 19 to the supply tube 4 to a blood treatment device.

A seventh conduit 26 has a first end connected to an inlet of the blood chamber of the pressure-measuring chamber 19 and a second end opening at the upper rim 32 of the upper edge of the flat body 16. The second end of the seventh conduit 26 is fitted with a socket 59 in which a first end of a pre-dilution infusion tube 9 is received and glued. The fluid distribution module 1 shown in FIG. 3 therefore allows for infusion of a medical liquid in the extracorporeal blood circuit upstream and downstream of a blood treatment device (pre- and post-dilution).

The right lateral edge of the flat body 16 includes a recessed rim 37 and a protruding rim 38, and the sixth conduit 25 has a first end connected to an inlet of the blood chamber of the pressure-measuring chamber 19, and a second end opening at a portion of rim connecting the recessed rim 37 to the protruding rim 38 of the right lateral edge of the flat body 16.

Figure 5:
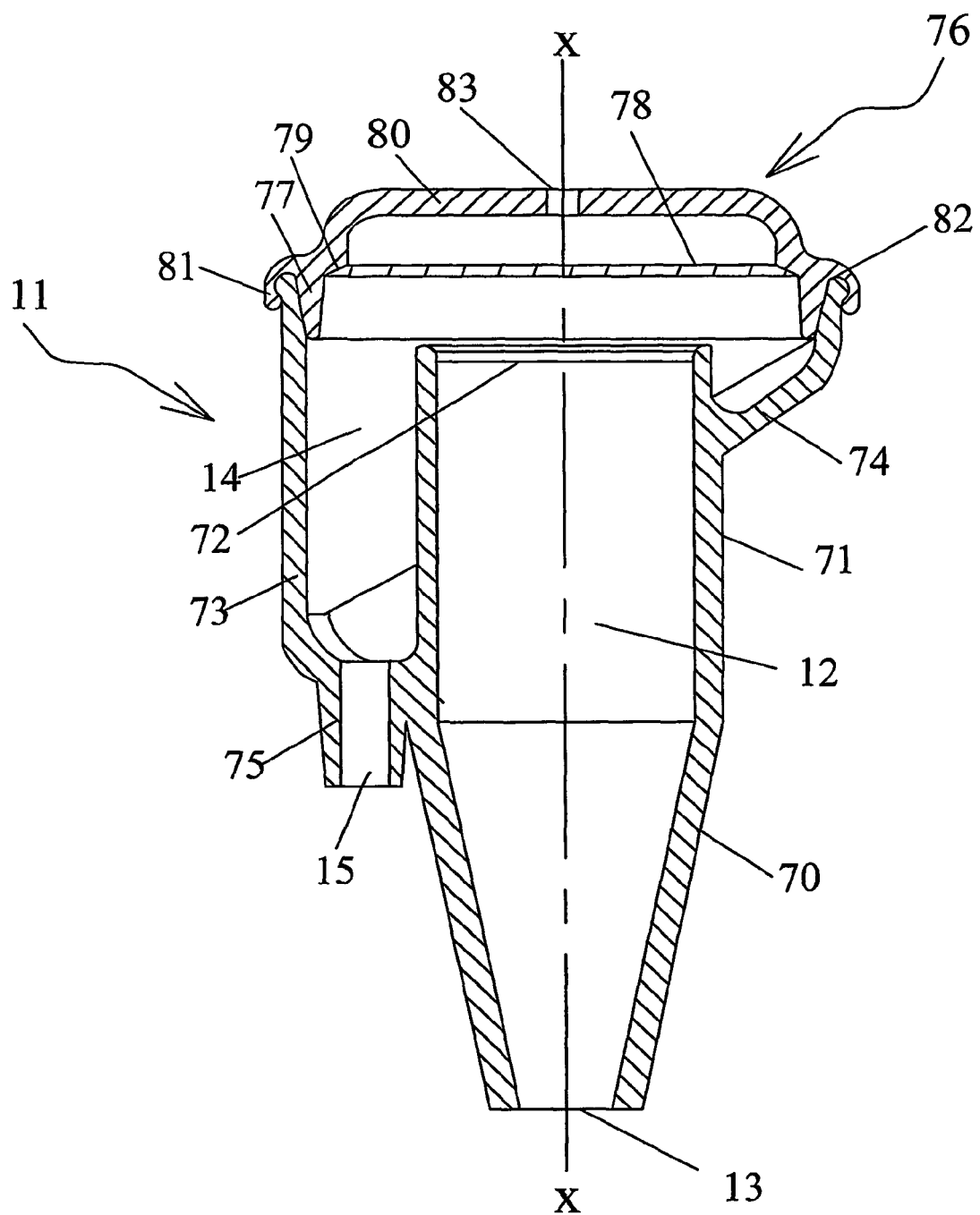
FIG. 5 is a first cross section view of the degassing device of the extracorporeal blood circuit of either of FIGS. 1 to 3, the cross section being along a plane containing a central longitudinal axis of the degassing device and parallel to the sheet of drawing.
Figure 6:
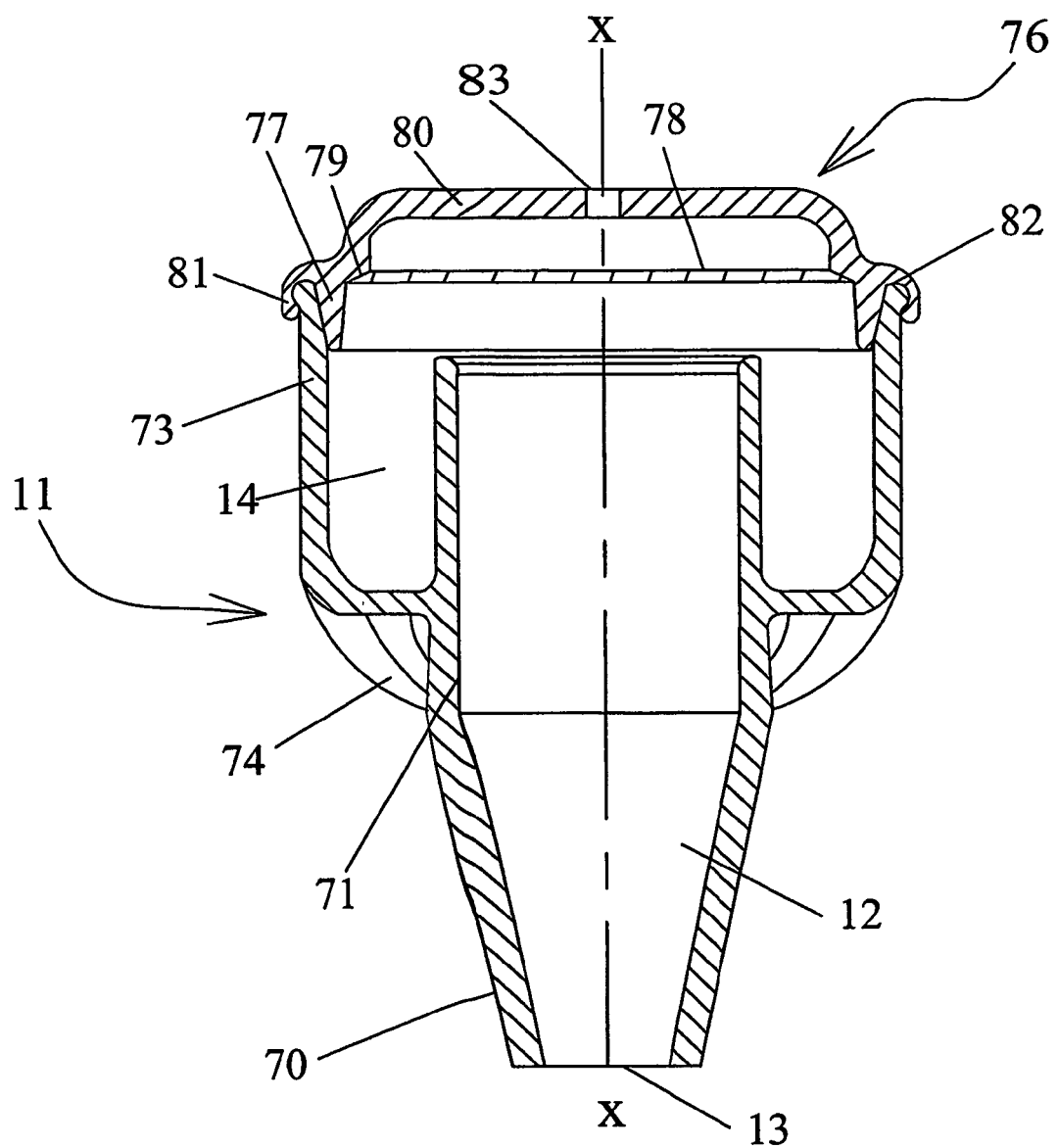
FIG. 6 is a second cross section view of the degassing device of the extracorporeal blood circuit of either of FIGS. 1 to 3, the cross section being along a plane containing a central longitudinal axis of the degassing device and perpendicular to the sheet of drawing.
Figure 7:
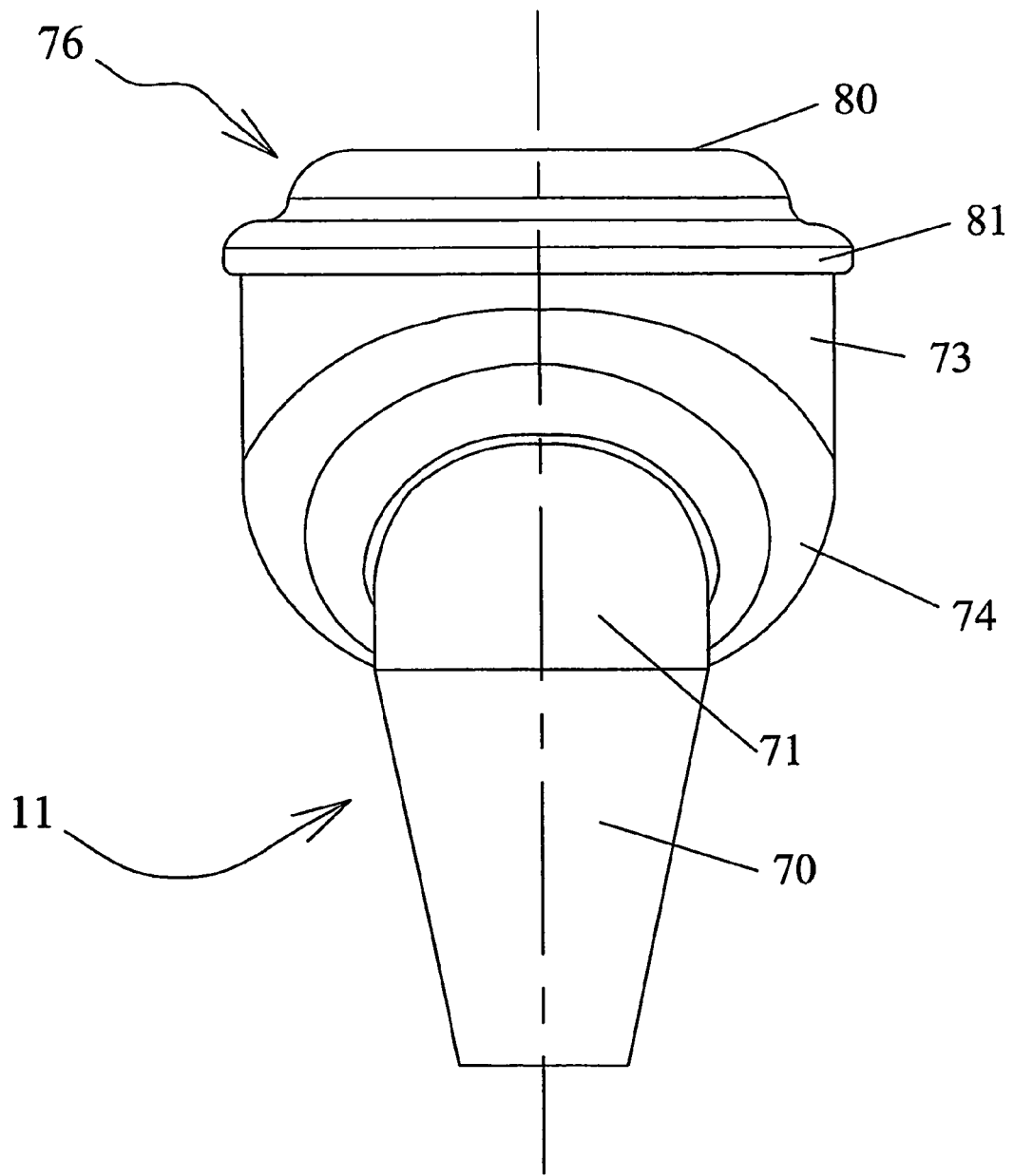
FIG. 7 is a side view of the degassing device of either of FIGS. 1 to 3.

The blood-degassing device 11 of the distribution module 1 is shown in detail in the FIGS. 5, 6, 7.

In the direction of flow, the first chamber 12 of the degassing device 11 comprises an upstream portion delimited by a flaring frusto-conical wall 70 and a downstream portion delimited by a cylindrical wall 71 connected to the frusto-conical wall 70. Both portions of the first chamber 12 are centered on the longitudinal axis x of the degassing device 11, which, as mentioned above, is substantially vertical when the degassing chamber 11 is in an operational position. The lower rim of the frusto-conical wall 70 defines the inlet 13 of the degassing device 11. The upper rim of the cylindrical wall 71 defines an opening or passageway 72 between the first chamber 12 and the second chamber 14.

In the direction of flow, the second chamber 14 of the degassing device 11 comprises a disk-shaped upstream portion extending above the passageway 72 and a downstream portion extending below the passageway 72 and partially and asymmetrically surrounding the downstream portion of the first chamber 12. The downstream portion of the second chamber 14 is delimited by a cylindrical wall 73 that is concentric to the cylindrical wall 71 of the first chamber 12, and by a substantially flat bottom wall 74 that is beveled of about 45 degrees with respect to the axis x. The highest point of the oblique bottom wall 74 is adjacent to the rim of the cylindrical wall 73. It results from the respective arrangement of the first chamber 12 and of the downstream portion of the second chamber 14 that the second chamber 14 forms an overflow for a liquid flowing from the first chamber 12 into the second chamber 14. The outlet port 15 of the degassing device 11 comprises a tubular wall 75 that is connected to the bottom wall 74 of the second chamber 14, at the lowest point thereof. The outlet port 15 extends downwards from the bottom wall 74 and its central axis is substantially parallel to the central axis x of the degassing device 11.

It results from the shape of the second chamber 14 (cylindrical wall 73 connected to a slanting bottom wall 74), and from the connection of the outlet port 15 at the lowest point thereof, two characteristics that are of particular interest for a degassing device intended for blood: in comparison to a second chamber that would completely and symmetrically surround the first chamber or even only the upstream cylindrical portion of the first chamber, with a bottom wall substantially perpendicular to the longitudinal axis of the degassing device, the design represented in the figures allows for a degassing device having a minimal internal volume, and in which there is no area of relative stagnation for a liquid circulated through the degassing device. It was observed during the research work that led to the present invention, that with a second chamber completely surrounding the first chamber, with a bottom wall substantially perpendicular to the longitudinal axis of the degassing device, an area of relative stagnation appears in the second chamber opposite to the outlet port.

The disk-shaped upstream portion of the second chamber 14 is defined within a capsule like lid 76 fitting on the upper rim of the cylindrical wall 73 of the second chamber 14. More specifically, the disk-shaped upstream portion of the second chamber 14 is delimited by an inner peripheral wall 77 of the lid 76, which has a frusto-conical inner surface, and by a circular hydrophobic membrane 78 closing an opening of the second chamber 14 within the lid 76 defined by an inner annular shoulder 79. The hydrophobic membrane 78 is secured (e.g. by gluing) at its periphery to the shoulder 79 and is perpendicular to the axis x of the degassing device 11. In more details, the capsule like lid 76 comprises a circular flat top wall 80 connected to the inner peripheral wall 77 and to an outer peripheral wall 81. The inner peripheral wall 77 and the outer peripheral wall 81 define therebetween a groove 82 corresponding to the upper rim of the cylindrical wall 73 of the second chamber 14, so that the lid 76 can be engaged into the rim of the cylindrical wall 73 and secured thereto, e.g. by gluing. The lid 76 also comprises a vent 83 in the middle of the circular flat top wall 79. The annular shoulder 79 is spaced apart from the top wall 80 of the lid 76 so that the hydrophobic membrane 78 can deform under positive pressure. The top wall 80 of the lid 76 essentially protects the hydrophobic membrane 78 against outside blows.

It results from the respective arrangement of the first chamber 12 and of the of the second chamber 14 that a liquid circulated through the degassing device 11 has an umbrella pattern with a longitudinal component within the first chamber 12 and a radial component within the upstream portion of the second chamber 14. The radial component of the flow tangentially sweeps the hydrophobic membrane 76 and helps prevent the formation of blood foam along its internal surface while keeping bubbles and micro bubbles in constant motion along the membrane until they escape therethrough.

Its is possible to optimize the efficiency of the degassing device of the invention by selecting the diameter of the downstream cylindrical part of the first chamber 12 (wall 71) with respect to the maximal flow rate of blood within the extracorporeal blood circuit, as well as the size of the second chamber 14 (diameter of the cylindrical wall 73) with respect to the size of the first chamber 12 (diameter of the cylindrical wall 71) so that:

the maximal velocity of the liquid in the first chamber 12 (corresponding the maximal flow rate in the extracorporeal blood circuit) is never high enough to prevent the bubbles and micro-bubbles from migrating towards the hydrophobic membrane 78 and to expel them to the outlet port 15;

the velocity of the liquid entering the second chamber decreases to such an extent that bubbles and micro-bubbles can migrate buy gravity towards the hydrophobic membrane 78.

For example, for a maximal blood flow rate of about 500 ml/min within the extracorporeal blood circuit, it was determined during the researches that led to the invention that an optimal velocity of blood within the downstream portion of the first chamber 12 (cylindrical wall 71) should be less than about 3 m/min and that the optimal ratio of the velocity of blood within the downstream portion of the first chamber 12 to the velocity of blood within the second chamber 14 at the level of the passageway 72 should be at least about 2.

A prototype of the degassing device 11 was made of molded polycarbonate: the diameter of the downstream portion of the first chamber 12 (cylindrical wall 71) was 16 mm; the inner diameter of the second chamber 14 at the level of the passageway 72 was 19 mm; the outer diameter of the second chamber 14 at the level of the passageway 72 was 32 mm; the diameter of the hydrophobic membrane 76 (useful surface) was 27 mm; the distance between the passageway 72 and the hydrophobic membrane 76 was 5 mm. The membrane was made of polytetrafluoroethylene and had a thickness of 0.13 mm and a pore size of 0.2 μm.

Bovine blood was circulated at a flow rate of 500 ml/mn in a closed loop circuit including a hemofilter connected to the prototype of degassing device 11. The velocity of blood within the degassing device was:

2.5 m/min in the downstream cylindrical portion of the first chamber 12;

2 m/min between the passageway 72 and the hydrophobic membrane 76;

1 m/min in the downstream portion of the second chamber 14, just below the level of the passageway 72; and 2 m/min in the downstream portion of the second chamber 14, just upstream of the outlet port 15.

The pressure in the degassing device was 50 mmHg. After four hours, 5 ml of air was injected in the circuit upstream of the hemofilter. After 15 minutes, the air injected in the circuit had been totally removed by the degassing device 11.

Figure 8:
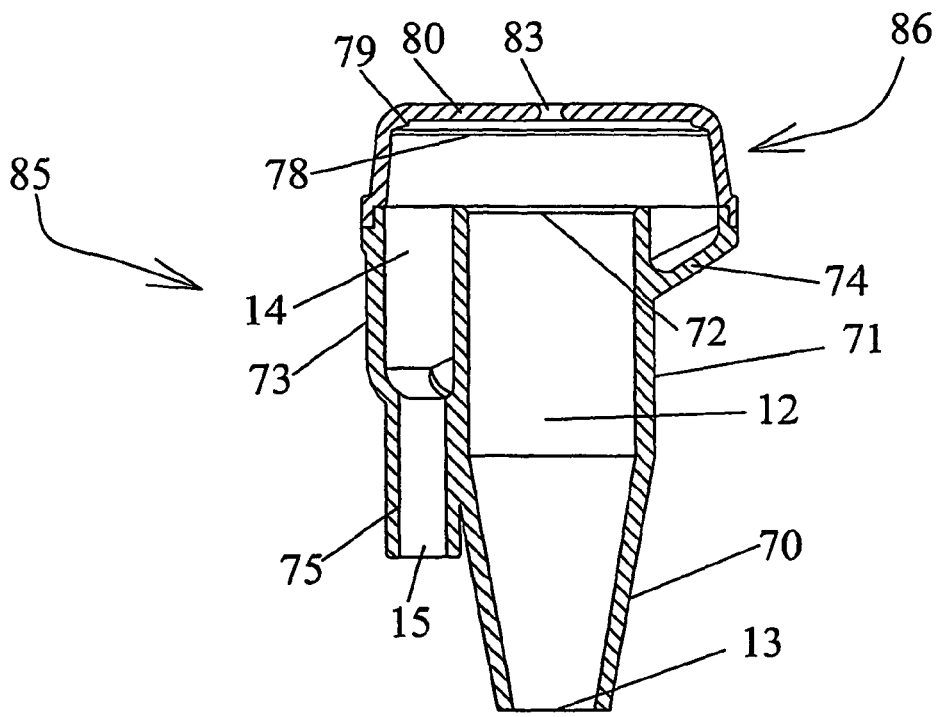
FIG. 8 is a cross section view of a second embodiment of a degassing device for an extracorporeal blood circuit according to the invention.
Figure 9:
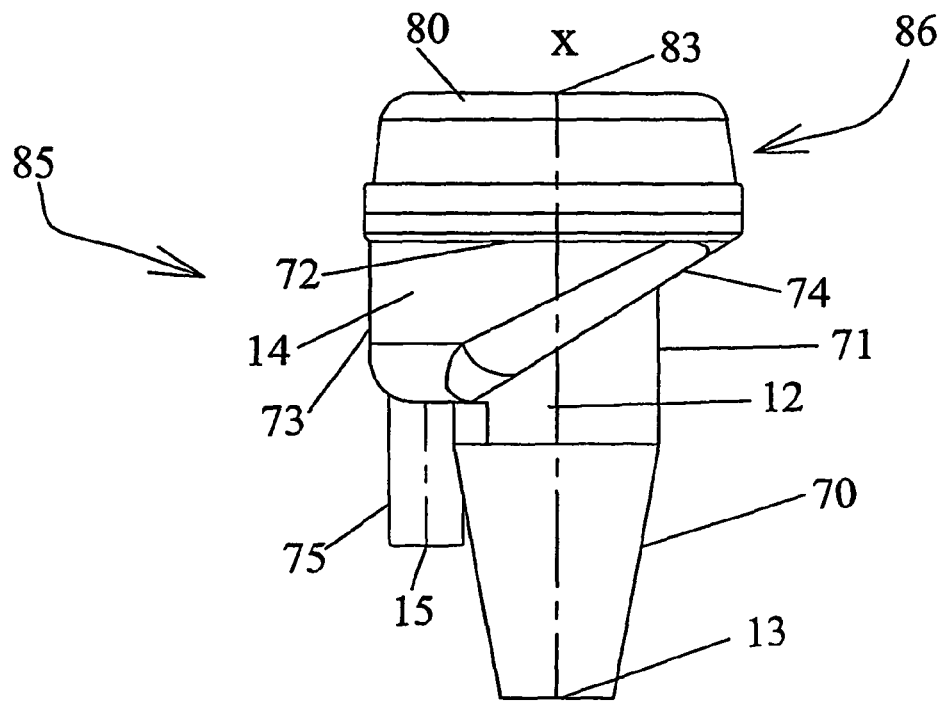
FIG. 9 is a front view of the degassing device shown in FIG. 8.

FIGS. 8 and 9 show a degassing device 85 that can be mounted in the fluid distribution module of FIGS. 1 to 3 as a substitute for the degassing device 11.

The degassing device 85 differs from the degassing 11 essentially in the way the lid 86 connects to the cylindrical wall 73 delimiting the second chamber 14, and in the position of the hydrophobic membrane 78 within the lid 86. The lid 86 comprises a slightly frusto-conical wall 87 and a flat top wall 80.

The lower rim of the frusto-conical wall 87 of the lid 86 comprises an annular inner rabbet. The upper rim of the cylindrical wall 73 of the second chamber 14 comprises a corresponding outer annular rabbet so that the lid 86 can engage the cylindrical wall 73 and form therewith a tight joint. The rims of the lid 86 and of the cylindrical wall 73 are dimensioned so that when the lid 86 is engaged on the top of the circular wall 73 the inner surfaces thereof are flush.

Also, in the degassing device 85, the annular shoulder 79 to which the hydrophobic membrane 78 is secured within the lid 86 is close to the top wall 80 of the lid 86. The hydrophobic membrane 78 can deform under positive pressure until it abuts against the top wall 80 of the lid 86. The lid 76 therefore protects the hydrophobic membrane 78 not only against outside blows but also from high positive pressure.

The following materials are appropriate for manufacturing the blood extracorporeal circuit according to the invention:

The connecting structure 10 (i.e. the flat body 16, and the base portions 40 of the pressure measuring chambers 17, 18, 19 and the conduits 20, 21, 22, 23, 24, 25, 26 made integral therewith), the lids 41 of the pressure measuring chambers 17, 18, 19 and the degassing device 11 can be made of molded polycarbonate.

The flexible membranes 42 of the pressure measuring chambers 17, 18, 19 can be made of a blend of styrene ethylene and butylene styrene The hydrophobic membrane 76 can be made of polytetrafluoroethylene.

The various tubes 3, 4, 5, 6, 7, 8, 9 connected to the connecting structure 10 as well as the pump hose 2 can be made of polyvinyl chloride.

The operation of the extracorporeal blood circuit (FIG. 3) according to the invention in combination with a hemodialyzer is as follows.

Before a treatment session, the fluid distribution module 1 is secured to the front panel of a treatment machine (not shown) by engaging the two sockets 55, 56 and the stud 60 protruding on both lateral sides of the connecting structure 10 into three corresponding clamps of the blood treatment machine that hold the distribution module 1 a substantially vertical plan, with the degassing chamber 11 in the upper position. Three pressure sensors mounted in the treatment machine are connected via the gas measuring ports 50 to the three pressure-measuring chambers 17, 18, 19. The pump hose 2 is engaged between the rotor and the circular race of a peristaltic pump that is a part of the machine. The blood supply tube 4 is connected to the inlet of the blood compartment of a hemodialyzer and the blood discharge tube 7 is connected to the outlet of the blood compartment of the hemodialyzer. A bag of sterile saline solution is connected to the blood withdrawal (arterial) tube 5 and a waste collection bag is connected to the blood return (venous) tube 6. The sterile solution is pumped by the peristaltic pump from the sterile solution bag into the arterial tube 5, the second and third pressure-measurement chambers 18, 19, the blood supply tube 4, the blood compartment of the hemodialyzer, the blood discharge tube 7, the first pressure-measurement chamber 17, the degassing device 11 and the venous tube 6, to the waste collection bag, so as to rinse the extracorporeal blood circuit, to fill it with sterile saline solution and to remove air therefrom (preparatory steps of a treatment usually called "priming" of the extracorporeal blood circuit). At the end of this process, there is no more air in the degassing device 11. Then, the arterial tube 5 is connected to a blood vessel of a patient and blood is pumped into the extracorporeal circuit, which causes the saline solution to flow out of the venous tube 6 into the waste collection bag. When blood reaches the end of the venous tube 6, the venous tube 6 is in turn connected to a blood vessel of the patient and the treatment proper can start.

In the degassing device 11, blood enters the first chamber 12 via the inlet 13, flows through the first chamber 12, pours into the second chamber 14 and leaves the degassing device 11 via the outlet port 15. Since the cross-section of the second chamber 14 at the level of the passageway 72 is substantially larger than the cross-section of the passageway 72 proper, the blood flow substantially decreases when blood enters the second chamber 14. This helps the bubbles and microbubbles that may be present in blood to move upwards by gravity towards the hydrophobic membrane 76. Also, because blood is directed by the cylindrical wall 71 of the first chamber 12 towards the hydrophobic membrane 76 and from there towards the frusto-conical peripheral wall 77 of the lid 76, the overall flow pattern of blood is umbrella like with a component that is tangential to the hydrophobic membrane 78. The membrane 78 is therefore permanently swept and the creation of a static layer of blood foam on the inner surface of the membrane 78 is prevented. Instead, the bubble and microbubbles are kept in a permanent motion at the vicinity of the membrane 78, through which they pass shortly after entering the second chamber 14.

The various embodiments of the invention described above are only to exemplify the invention. The scope of the invention is therefore not limited to any of them.

The invention claimed is:

1. A fluid distribution module for causing and monitoring a circulation of fluids from and to a patient through an extracorporeal blood treatment device, comprising:

a degassing device comprising:

a first chamber having an inlet for a liquid;

a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway, and the second chamber comprises an upstream portion extending above the passageway and a downstream portion extending below the passageway; and a connecting structure having at least a first and a second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

2. A fluid distribution module according to claim 1, wherein the connecting structure further comprises a third conduit defined therein having a first end for connection to a post-dilution infusion tube and a second end connected to the first conduit.

3. A fluid distribution module according to claim 1, wherein the connecting structure further comprises a fourth and a fifth conduits defined therein, wherein the fourth conduit comprises a first end for connection to a blood withdrawal tube from a patient and a second end for connection to a first end of a pump hose of a peristaltic pump, and the fifth conduit comprises a first end for connection to a second end of the pump hose of a peristaltic pump and a second end for connection to a supply tube to a blood treatment device.

4. A fluid distribution module according to claim 3, wherein the connecting structure further comprises a sixth conduit defined therein having a first end for connection to an anti-coagulant tube and a second end connected to the fifth conduit.

5. A fluid distribution module according to claim 3, wherein the connecting structure further comprises a seventh conduit defined therein having a first end for connection to a pre-dilution infusion tube and a second end connected to the fourth conduit.

6. A fluid distribution module according to claim 3, wherein the connecting structure further comprises a second pressure-measuring chamber having a first and a second compartments separated by a flexible membrane, wherein the first compartment is connected to the fourth conduit, and the second compartment has a measuring port for connection to a gas pressure sensor.

7. A fluid distribution module according claim 3, wherein the connecting structure further comprises a third pressure-measuring chamber having a first and a second compartments separated by a flexible membrane, wherein the first compartment is connected to the fifth conduit, and the second compartment has a measuring port for connection to a gas pressure sensor.

8. A fluid distribution module according to claim 3, wherein the connecting structure further comprises:

a first pressure-measuring chamber having a first and a second compartments separated by a flexible membrane, wherein the first compartment is connected to the first conduit, and the second compartment has a measuring port for connection to a gas pressure sensor;

a second pressure-measuring chamber having a first and a second compartments separated by a flexible membrane, wherein the first compartment is connected to the fourth conduit, and the second compartment has a measuring port for connection to a gas pressure sensor; and a third pressure-measuring chamber having a first and a second compartments separated by a flexible membrane, wherein the first compartment is connected to the fifth conduit, and the second compartment has a measuring port for connection to a gas pressure sensor, wherein the measuring ports of the first, second, and third pressure-measuring chambers have a central axis, and the central axes of at least two of the measuring ports are substantially parallel.

9. A fluid distribution module according to claim 3, wherein the connecting structure further comprises:

a first pressure-measuring chamber having a first and a second compartments separated by a flexible membrane, wherein the first compartment is connected to the first conduit, and the second compartment has a measuring port for connection to a gas pressure sensor;

a second pressure-measuring chamber having a first and a second compartments separated by a flexible membrane, wherein the first compartment is connected to the fourth conduit, and the second compartment has a measuring port for connection to a gas pressure sensor; and a third pressure-measuring chamber having a first and a second compartments separated by a flexible membrane, wherein the first compartment is connected to the fifth conduit, and the second compartment has a measuring port for connection to a gas pressure sensor, wherein the central axes of the measuring ports of at least two of the first, second, and third pressure-measuring chambers are substantially perpendicular to a longitudinal axis of the degassing device.

10. A fluid distribution module according to claim 3, wherein the connecting structure comprises a first and second sockets forming the second end of the fourth conduit and the first end of the fifth conduit, wherein the first and second sockets are so positioned that a pump hose having both ends received in the two sockets forms a loop that laterally extends within a plan from the connecting structure.

11. A fluid distribution module according to claim 1, wherein the connecting structure further comprises a first pressure-measuring chamber having a first and a second compartments separated by a flexible membrane, wherein the first compartment is connected to the first conduit, and the second compartment has a measuring port for connection to a gas pressure sensor.

12. A fluid distribution module according to claims 1, wherein the connecting structure has a periphery and comprises at least one socket connected thereto, wherein the socket has a recess for receiving one end of a tube and forms one end of one of the conduits defined within the connecting structure.

13. A fluid distribution module according to claim 1, wherein the first chamber of the degassing device has a downstream portion having a cross-section selected with respect to a maximal blood flow rate in an extracorporeal blood circuit connected to the degassing device so that the velocity of blood in the downstream portion of the first chamber is less than a predetermined velocity.

14. A fluid distribution module according to claim 13, wherein the cross-section of the downstream portion of the first chamber is selected with respect to a maximal blood flow rate in an extracorporeal blood circuit of about 500 ml/min so that the velocity of blood in the downstream portion of the first chamber is less than about 3 m/min.

15. A fluid distribution module according to claim 1, wherein the cross-section of the second chamber of the degassing device at the level of the passageway is selected so that the ratio of the velocity of blood within a downstream portion of the first chamber to the velocity of blood within the second chamber at the level of the passageway is more than a determined value.

16. A fluid distribution module according to claim 15, wherein the cross-section of the second chamber of the degassing device at the level of the passageway is selected so that the ratio of the velocity of blood within the downstream portion of the first chamber to the velocity of blood within the second chamber at the level of the passageway is at least about 2.

17. A fluid distribution module according to claim 1, wherein the downstream portion of the second chamber of the degassing device asymmetrically surrounds an upper part of the first chamber.

18. A fluid distribution module according to claim 17, wherein the first chamber comprises a downstream portion having a cylindrical wall extending along a longitudinal axis of the degassing device, and the downstream portion of the second chamber comprises a cylindrical wall partially surrounding the cylindrical wall of the first chamber and a bottom wall that is beveled with respect to the longitudinal axis of the degassing device.

19. A fluid distribution module according to claim 18, wherein the cylindrical wall of the first chamber and the cylindrical wall of the second chamber are concentric.

20. A fluid distribution module according to claim 1, wherein the passageway has a lesser cross-section than a cross-section of the second chamber so that a flow of liquid from the first chamber into the second chamber decreases within the second chamber.

21. A fluid distribution module according to claim 1, wherein the first chamber, the second chamber and the passageway are arranged with respect to each other so that a flow pattern of a liquid flowing through the degassing device comprises a component that is tangential to the hydrophobic membrane.

22. A fluid distribution module according to claim 1, wherein the flow pattern of a liquid flowing through the degassing device comprises an umbrella like component.

23. A fluid distribution module according to claim 1, wherein the first chamber, the second chamber and the passageway are arranged with respect to each other so that a liquid flowing through the degassing device keeps gas bubbles in motion along an inner surface of the hydrophobic membrane.

24. A fluid distribution module according to claim 1, wherein the first chamber comprises a downstream portion having a cross-section that is substantially the same as the cross-section of the passageway between the first and the second chambers.

25. A fluid distribution module according to claim 1, characterized in that the downstream portion of second chamber forms an overflow for a liquid flowing from the first chamber into the second chamber.

26. A fluid distribution module according to claim 1, wherein the upstream portion of the second chamber has a decreasing cross-section, with a larger cross-section that is substantially level with the passageway and a smaller cross-section that is substantially level with the hydrophobic membrane.

27. A fluid distribution module according to claim 1, wherein the outlet opens in the second chamber at a lowest point thereof.

28. An extracorporeal blood circuit comprising:
a fluid distribution module according to one of the claims 3 to 27;
a pump hose having a first end connected to the second end of the fourth conduit and a second end connected to the a first end of the fifth conduit;
a blood withdrawal tube connected to a first end of the fourth conduit;
a supply tube to a blood treatment device connected to the second end of the fifth conduit;
a discharge tube from a treatment device connected to the first end of the first conduit; and
a blood return tube connected to the second end of the second conduit.

29. A fluid distribution module for causing and monitoring a circulation of fluids from and to a patient through an extracorporeal blood treatment device, comprising:
a degassing device comprising:
a first chamber having an inlet for a liquid;
a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid,
wherein the first chamber partially extends within the second chamber and communicates therewith by an upper passageway, and the second chamber comprises an upstream portion extending above the passageway and a downstream portion extending below the passageway; and
a connecting structure having at least first, second, fourth and fifth conduits defined therein, wherein:
the first conduit comprises a first end for connection to a discharge tube from the treatment device and a second end connected to the inlet of the first chamber of the degassing device,
the second conduit comprises a first end connected to the outlet of the second chamber of the degassing device and a second end for connection to a blood return tube to a patient,
the fourth conduit comprises a first end for connection to a blood withdrawal tube from a patient and a second end for connection to a first end of a pump hose of a peristaltic pump,
the fifth conduit comprises a first end for connection to a second end of the pump hose of a peristaltic pump and a second end for connection to a supply tube to a blood treatment device, and
the second end of the fourth conduit and the first end of the fifth conduit are so positioned that a pump hose connected thereto forms a loop that laterally extends within a plan from the connecting structure.

30. A fluid distribution module for causing and monitoring a circulation of fluids from and to a patient through an extracorporeal blood treatment device, comprising:
a degassing device comprising:
a first chamber having an inlet for a liquid;
a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway, and the first chamber has a downstream portion having a cross-section selected with respect to a maximal blood flow rate in an extracorporeal blood circuit connected to the degassing device so that a velocity of blood in the downstream portion of the first chamber is less than a predetermined velocity; and a connecting structure having at least a first and a second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

31. A fluid distribution module for causing and monitoring a circulation of fluids from and to a patient through an extracorporeal blood treatment device, comprising:

a degassing device comprising:

a first chamber having an inlet for a liquid;

a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway, and the cross-section of the second chamber of the degassing device at the level of the passageway is selected so that the ratio of a velocity of blood within a downstream portion of the first chamber to a velocity of blood within the second chamber at the level of the passageway is more than a determined value; and a connecting structure having at least a first and a second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

32. A fluid distribution module for causing and monitoring a circulation of fluids from and to a patient through an extracorporeal blood treatment device, comprising:

a degassing device comprising:

a first chamber having an inlet for a liquid;

a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway, the second chamber comprises an upstream portion extending above the passageway and a downstream portion extending below the passageway, and the downstream portion of the second chamber of the degassing device asymmetrically surrounds an upper part of the first chamber; and a connecting structure having at least first and second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

33. A fluid distribution module for causing and monitoring a circulation of fluids from and to a patient through an extracorporeal blood treatment device, comprising:

a degassing device comprising:

a first chamber having an inlet for a liquid;

a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway that has a lesser cross-section than a cross-section of the second chamber so that a flow of liquid from the first chamber into the second chamber decreases within the second chamber; and a connecting structure having at least a first and a second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

34. A fluid distribution module for causing and monitoring a circulation of fluids from and to a patient through an extracorporeal blood treatment device, comprising:

a degassing device comprising:

a first chamber having an inlet for a liquid;

a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid, wherein the first chamber partially extends within the second chamber and communicates therewith by an upper passageway, and the first chamber, the second chamber and the passageway are arranged with respect to each other so that a flow pattern of a liquid flowing through the degassing device comprises a component that is tangential to the hydrophobic membrane; and a connecting structure having at least a first and a second conduits defined therein, wherein:

the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

35. A fluid distribution module for causing and monitoring a circulation of fluids from and to a patient through an extracorporeal blood treatment device, comprising:
 a degassing device comprising:
  a first chamber having an inlet for a liquid;
  a second chamber having a lid including a vent, a deformable hydrophobic membrane closing an opening of the second chamber within the lid, and an outlet for discharging the liquid, the hydrophobic membrane being allowed to deform under pressure until the membrane contacts a top wall of the lid,
  wherein the first chamber partially extends within the second chamber and communicates therewith by an upper passageway, and the first chamber, the second chamber and the passageway are arranged with respect to each other so that a liquid flowing through the degassing device keeps gas bubbles in motion along an inner surface of the hydrophobic membrane; and
 a connecting structure having at least a first and a second conduits defined therein, wherein:
  the first conduit comprises a first end for connection to a discharge tube from the treatment device and a second end connected to the inlet of the first chamber of the degassing device, and
  the second conduit comprises a first end connected to the outlet of the second chamber of the degassing device and a second end for connection to a blood return tube to a patient.

36. A fluid distribution module for causing and monitoring a circulation of fluids from and to a patient through an extracorporeal blood treatment device, comprising:
 a degassing device comprising:
  a first chamber having an inlet for a liquid;
  a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid,
  wherein the first chamber partially extends within the second chamber and communicates therewith by an upper passageway, the second chamber comprises an upstream portion extending above the passageway and a downstream portion extending below the passageway, and the downstream portion of second chamber forms an overflow for a liquid flowing from the first chamber into the second chamber; and
 a connecting structure having at least a first and a second conduits defined therein, wherein:
  the first conduit comprises a first end for connection to a discharge tube from the treatment device and a second end connected to the inlet of the first chamber of the degassing device, and
  the second conduit comprises a first end connected to the outlet of the second chamber of the degassing device and a second end for connection to a blood return tube to a patient.

37. A fluid distribution module for causing and monitoring a circulation of fluids from and to a patient through an extracorporeal blood treatment device, comprising:
 a degassing device comprising:
  a first chamber having an inlet for a liquid;
  a second chamber having a lid including a vent, a hydrophobic membrane closing an opening of the second chamber within the lid, and an outlet for discharging the liquid, the hydrophobic membrane being allowed to deform under pressure until the membrane contacts a top wall of the lid,
  wherein the first chamber partially extends within the second chamber and communicates therewith by an upper passageway, the second chamber comprises an upstream portion extending above the passageway and a downstream portion extending below the passageway, and the upstream portion of the second chamber has a decreasing cross-section, with a larger cross-section that is substantially level with the passageway and a smaller cross-section that is substantially level with the hydrophobic membrane; and
 a connecting structure having at least a first and a second conduits defined therein, wherein:
  the first conduit comprises a first end for connection to a discharge tube from the treatment device and a second end connected to the inlet of the first chamber of the degassing device, and
  the second conduit comprises a first end connected to the outlet of the second chamber of the degassing device and a second end for connection to a blood return tube to a patient.

\* \* \* \* \*

UNITED STATES PATENT AND TRADEMARK OFFICE
CERTIFICATE OF CORRECTION

| | |
|---|---|
| PATENT NO. | : 8,142,383 B2 |
| APPLICATION NO. | : 10/595705 |
| DATED | : March 27, 2012 |
| INVENTOR(S) | : Jürgen Dannenmaier et al. |

It is certified that error appears in the above-identified patent and that said Letters Patent is hereby corrected as shown below:

"Assignee: GAMBRO AB", should read --Assignee: GAMBRO LUNDIA AB--.

Signed and Sealed this
Thirty-first Day of July, 2012

David J. Kappos
*Director of the United States Patent and Trademark Office*